(12) United States Patent
Prud'Homme (10) Patent No.: US 8,813,562 B2
(45) Date of Patent: Aug. 26, 2014

(54) RELATIVE HUMIDITY SENSOR APPARATUS

(76) Inventor: Guy Prud'Homme, Mont-Royal (CA)

( * ) Notice: Subject to any disclaimer, the term of this patent is extended or adjusted under 35 U.S.C. 154(b) by 378 days.

(21) Appl. No.: 13/165,004

(22) Filed: Jun. 21, 2011

(65) Prior Publication Data

US 2011/0314908 A1 Dec. 29, 2011

Related U.S. Application Data

(60) Provisional application No. 61/358,470, filed on Jun. 25, 2010.

(51) Int. Cl.
*G01N 19/00* (2006.01)
*G01N 25/62* (2006.01)

(52) U.S. Cl.
CPC ................................. *G01N 25/62* (2013.01)
USPC ............................................ 73/335.08

(58) Field of Classification Search
USPC ............................ 73/335.08; 374/28
See application file for complete search history.

(56) References Cited

U.S. PATENT DOCUMENTS

| 1,557,163 A | * | 10/1925 | Hodge | ......................... 73/335.07 |
| 2,894,391 A | * | 7/1959 | Colt et al. | ................... 73/335.09 |
| 4,129,250 A | * | 12/1978 | Chaikin et al. | ............... 236/44 A |

* cited by examiner

*Primary Examiner* — Peter Macchiarolo
*Assistant Examiner* — Tamiko Bellamy
(74) *Attorney, Agent, or Firm* — Norton Rose Fulbright Canada LLP (57) ABSTRACT

A sensor apparatus measures wet-bulb temperature. The sensor apparatus comprises a casing. A measuring device comprises a sock at its probe end. A washing unit having a fluid outlet in the casing projects a fluid on the sock to remove residue and to humidify the sock. An actuator displaces the measuring device between a washing position and a measuring position. In the washing position, the sock is in register with the washing unit in the casing. In the measuring position, the measuring device has the sock out of the casing and away from the washing unit to measure an ambient wet-bulb temperature. A method for measuring a wet-bulb temperature is also provided.

13 Claims, 8 Drawing Sheets

RELATIVE HUMIDITY SENSOR APPARATUS

CROSS-REFERENCE TO RELATED APPLICATION

The present application claims priority on U.S. Provisional Patent Application No. 61/358,470, filed on Jun. 25, 2010, and incorporated herein by reference.

FIELD OF THE APPLICATION

The present application relates to the measurement of parameters such as temperature and relative humidity, and more particularly to the measurement of such parameters in high-temperature industrial environments.

BACKGROUND OF THE ART

One known method for determining relative humidity consists in looking up a psychrometric chart knowing the dry bulb temperature and wet bulb temperature. To measure wet bulb temperature, a thermometer (e.g., thermocouple) has its bulb wrapped in a cloth (i.e., sock) that is kept wet with water via wicking action. Such an instrument is called a wet bulb thermometer.

In practice, numerous conditions must be met in order to ensure the precision of the reading obtained with the wet bulb thermometer, notably to protect the sock from dust, and ensuring that the sock is always humid. For instance, the wet bulb temperature reading must be taken when the water on the sock is at the wet bulb temperature of the air. Therefore, systems have been developed for industrial applications to continously feed water to the sock. However, the feed of water may saturate the sock with water, not allowing the water of the sock to warm up to the wet-bulb temperature of the air. Moreover, in industrial applications such as in driers, ovens, or the like, in which there may be a non-negligible amount of airborne dust particles resulting from a process, the readings obtained from the wet bulb thermometer may be affected if a crust of dust particles forms on the sock.

SUMMARY OF THE APPLICATION

It is therefore an aim of the present invention to provide a relative humidity sensor apparatus that addresses issues associated with the prior art.

Therefore, in accordance with the present application, there is provided a sensor apparatus for measuring wet-bulb temperature, comprising: a casing; a measuring device comprising a sock at its probe end; a washing unit having at least one fluid outlet in the casing for projecting a fluid on the sock to remove residue and to humidify the sock; and an actuator displacing the measuring device between a washing position in which the sock is in register with the washing unit in the casing, and a measuring position in which the measuring device has the sock out of the casing and away from the washing unit to measure an ambient wet bulb temperature.

Further in accordance with the present disclosure, there is provided a method for measuring at least a wet-bulb temperature, comprising: humidifying a sock of a measuring sensor and positioning the sock in an environment in which the wet-bulb temperature is monitored; measuring the wet-bulb temperature; identifying an effective wet-bulb temperature by monitoring a rate of change of the wet-bulb temperature to detect a low change threshold simultaneously with the measuring; and identifying a dry condition of the sock by monitoring a rate of change of the wet-bulb temperature to detect a high change threshold simultaneously with the measuring and sequentially after the low change threshold.

DESCRIPTION OF THE PREFERRED EMBODIMENTS

Figure 1:
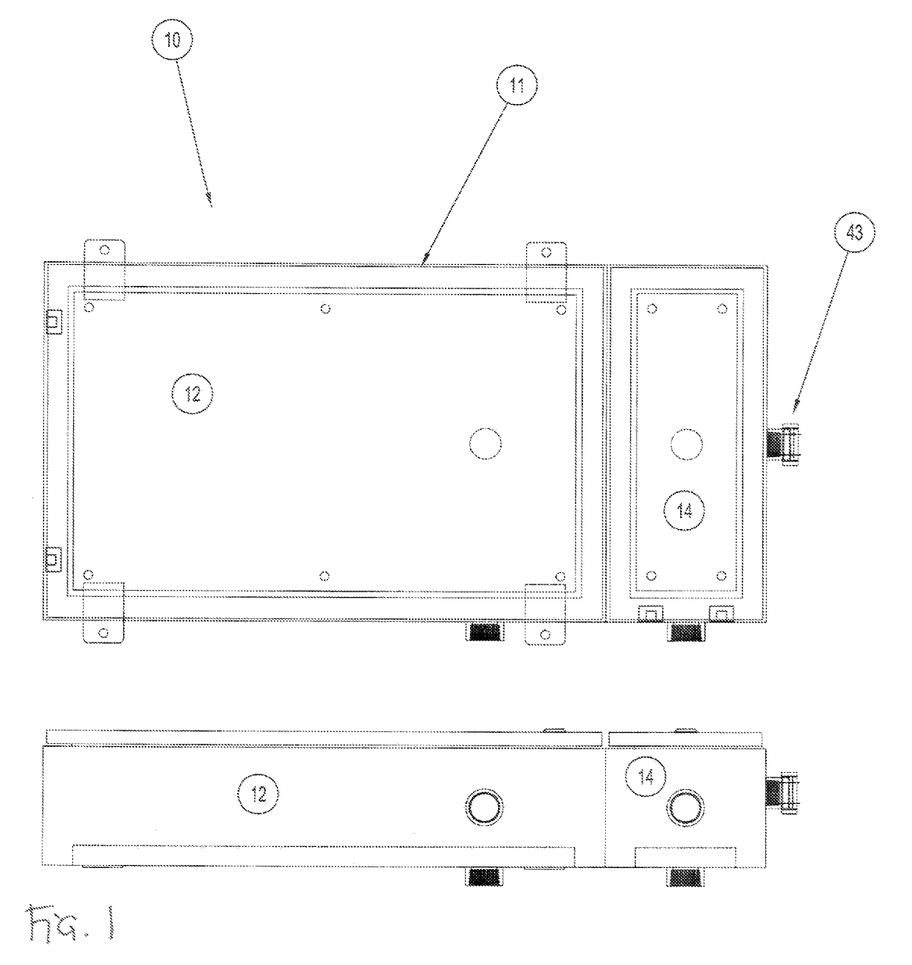
FIG. 1 is a top plan view of a relative-humidity sensor apparatus in accordance with the present invention, with covers thereon.
Figure 2:
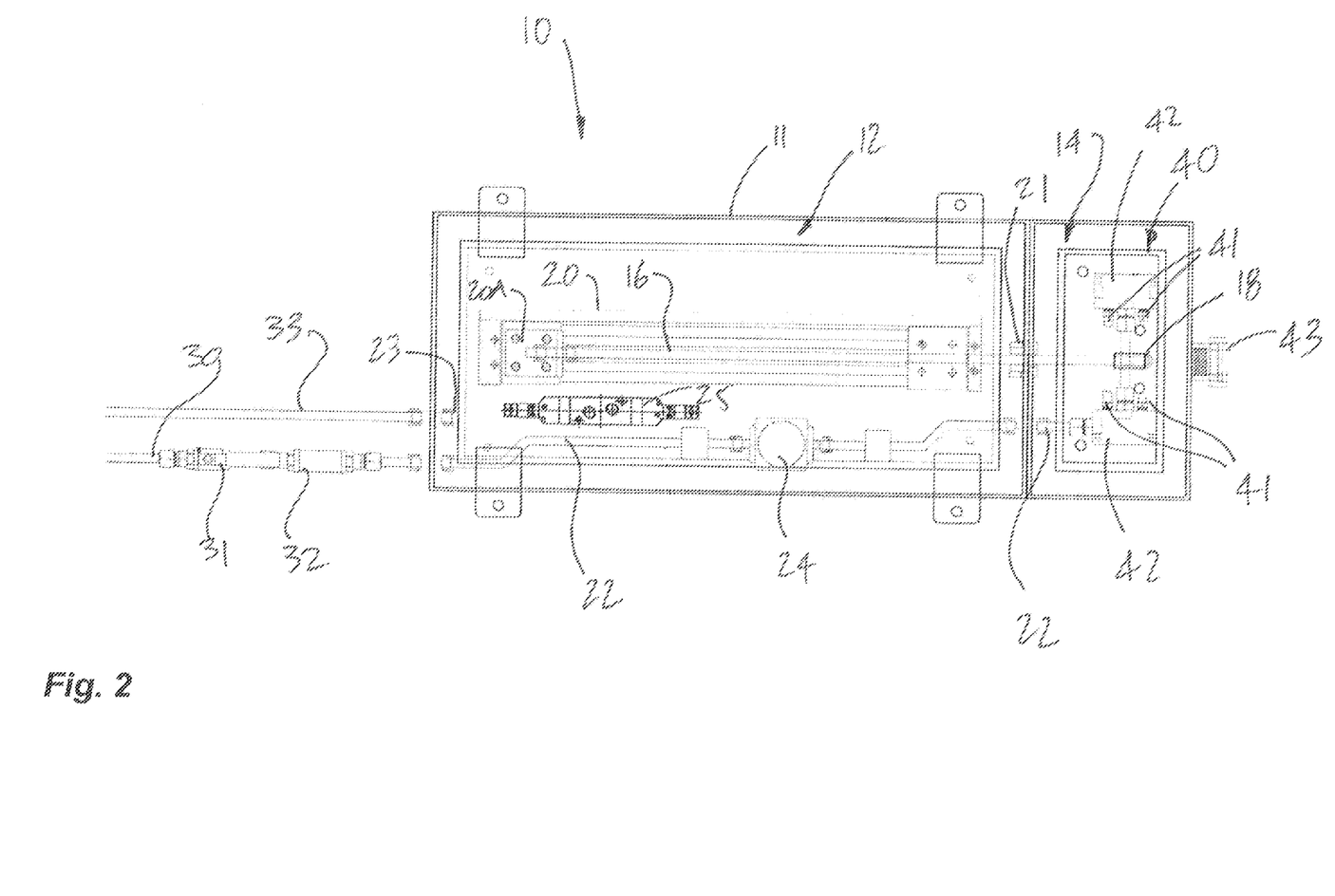
FIG. 2 is a top plan view of the relative-humidity sensor apparatus of FIG. 1, with the covers removed and a thermocouple in a washing position.
Figure 3:
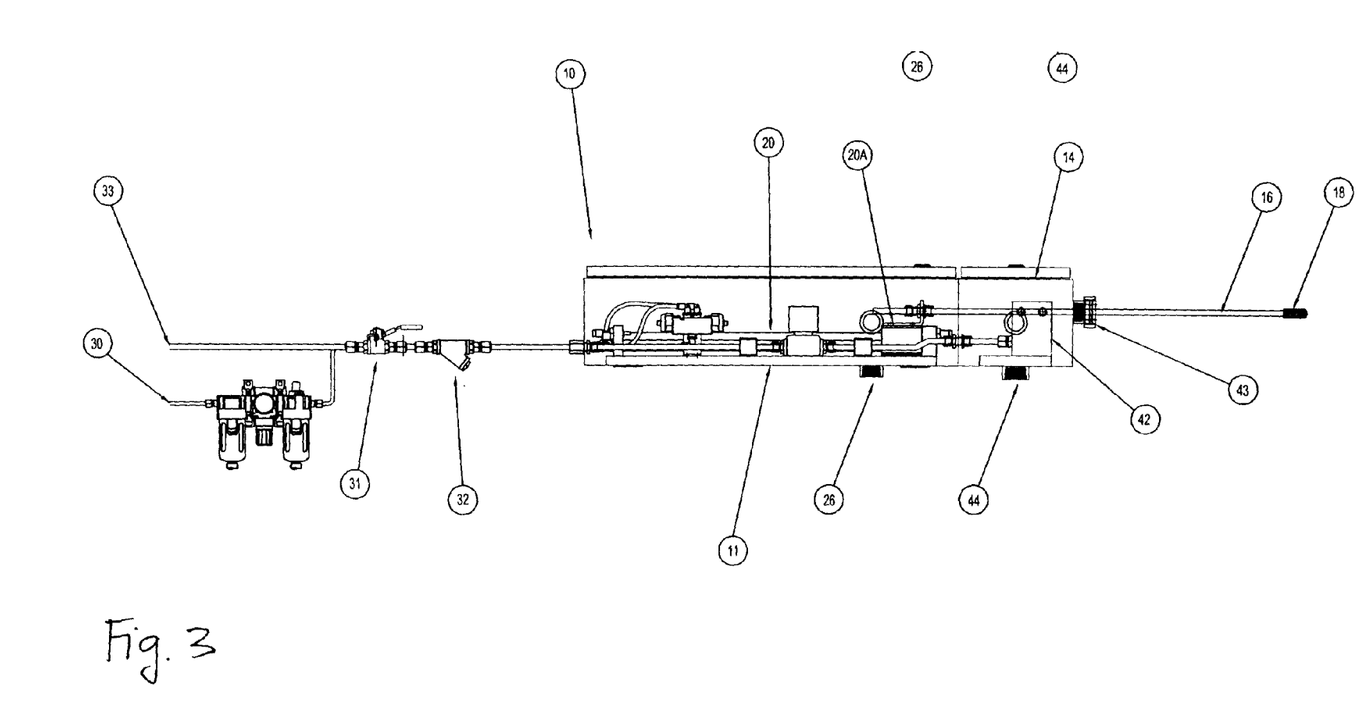
FIG. 3 is a side elevation view of the relative-humidity sensor apparatus of FIG. 1.

Referring to the drawings, and more particularly to FIGS. 1-3, there is illustrated a relative humidity sensor apparatus at 10 in accordance with the present disclosure. The sensor apparatus 10 is used to measure the relative humidity by measuring the wet bulb temperature and dry bulb temperature. The sensor apparatus 10 has a casing 11. The casing 11 is divided into two different compartments, namely a mechanical compartment 12 and a washing compartment 14. The casing 11 is for instance built according to NEMA 4 specifications, among other possibilities. As an alternative to having separate compartments, the components in the casing 11 may be individually sealed.

The mechanical compartment 12 encloses the actuator responsible for the movement of a thermocouple 16 between a measuring position and a washing position. Moreover, the mechanical compartment 12 may enclose various control components, such as valves, conduits, wires and the like. The dry bulb thermocouple may be separated from the sensor apparatus 10, or may alternatively be part of it. In order to protect the dry bulb thermocouple, the tip of the thermocouple may be covered with a thermowell.

The washing compartment 14 encloses components to wash the sock of the thermocouple 16 and keep it humid for wet bulb measurement purposes. As is shown in FIGS. 1 and 2, the thermocouple 16 has a sock 18 thereon that must be humid during the measurement of the wet bulb temperature. The thermocouple 16 (and the dry bulb thermocouple) may be a K-type thermocouple, connected to a controller that receives the microvolt signals therefrom. Any other type of thermocouple may be used as a function of the process, and other types of temperature measuring devices may be used as well as alternatives to thermocouples. The wires connecting the thermocouples and other electric components to a controller are preferably covered with a protective sheath.

The sock 18 may be retained at the end of the thermocouple 16, for instance using a snap ring or any appropriate connector. Materials that may be used for the sock 18 include kevlar and ceramic fiber. These materials can remain humid and can sustain the hostile process conditions to which the sock 18 will be subjected.

In the mechanical compartment 12, a linear actuator 20 is enclosed, to which the thermocouple 16 is connected for movement between the washing position and the measuring position. According to an embodiment, the linear actuator 20 may, for instance, be a magnetically-coupled rodless air cylinder displacing a carriage 20A to which an end of the thermocouple 16 is secured. Among various possibilities, the magnetically-coupled rodless air cylinder is a Parker™ P1Z series cylinder. Any other appropriate type of actuator may be used, such as a rack and pinion, mechanical arm, standard pneumatic or hydraulic cylinder or the like.

The magnetically-coupled rodless cylinder is efficient in terms of size and operational requirements (standard compressed air line). The course of the linear actuator 20 must be sufficient for the end of the thermocouple 16 to project out of the washing compartment 14, and possibly through the wall of the process equipment (e.g., oven), to reach an interior of the process equipment. In some instances, the process equipment has insulation layers, whereby the course of the linear actuator 20 must be sufficient to move beyond the insulation layers. In the event that the course of the linear actuator 20 is greater than required, proximity switches or the like may be used to detect the position of the carriage 20A of the linear actuator 20.

A guiding sleeve 21 communicates between the mechanical compartment 12 and the washing compartment 14, and supports an elongated body of the thermocouple 16 to control the motion of the thermocouple 16 between the washing position and the measuring position. The guiding sleeve 21 ensures that its junction with the thermocouple 16 is substantially air-tight and water-tight, to avoid water and dust infiltration in the mechanical compartment 12.

The guiding sleeve 21 may be threaded so as to be screwed to the wall separating the mechanical compartment 12 from the washing compartment 14. A sleeve of appropriate material is provided within the guiding sleeve 21 to reduce friction between the thermocouple 16 and the guiding sleeve 21. It is pointed out that the material used for the sleeve must be adapted to operate at high temperatures, and PTFE is a suitable material for some processes.

A rod-wiper seal may be provided on the guiding sleeve 21, in the washing compartment 14. The wiper seal 21B wipes dust and water off the thermocouple 16 when the thermocouple 16 moves from the measuring position to the washing position. Materials that are suited for the wiper seal in given temperature conditions include Viton™ and Teflon™ (of the high-temperature resistance type) among other possibilities. It is also considered to equip the guiding sleeve 21 with an appropriate seal, such as a bounded seal, between the guiding sleeve 21 and the body of the casing 11, to prevent any leaks.

The mechanical compartment 12 also encloses a water-supply line 22 and an air-supply line 23. Appropriate controls for these supply lines 22 and 23, such as a valves 24 and 25, may also be enclosed in the mechanical compartment 12.

The valve 24 is an on/off valve to block or actuate the water supply to a washing unit in the washing compartment 14, as described hereinafter. According to an embodiment, the valve 24 is a solenoid valve having a diaphragm, but any appropriate control valve may be used.

The valve 25 is a control valve used to direct the compressed air to one of the two ports of the linear actuator 20.

Referring to FIG. 3, a drain 26 is provided in a bottom of the mechanical compartment 12. Although it is not anticipated that water will reach the mechanical compartment 12, the drain 26 is provided in case of leaks in the water-supply line 22. The drain 26 may be connected to a drain pipe having a check valve therein to block a backflow of water at the drain 26.

Referring to FIGS. 1-3, the water-supply line 22 is connected to a water-supply network via an exterior water-supply line 30. The exterior water-supply line 30 may be provided with controls as well, such as a valve 31 (e.g., a ball valve or any other appropriate valve) and possibly a strainer 32 to remove impurities from the water supply. The valve 31 is provided to stop the water supply to the sensor apparatus 10, for instance for maintenance purposes.

Similarly, an exterior air-supply tubing 33 is connected to the mechanical compartment 12 and thus to the air-supply line 23 within the mechanical compartment 12.

A washing unit 40 is enclosed in the washing compartment 14. The washing unit 40 is in fluid communication with the water-supply line 22, so as to produce a water spray using the jets 41. The jets 41 spray pressurized water on the sock 18 of the thermocouple 16, so as to remove any impurities, cool the thermocouple 16, and to subsequently humidify the sock 18.

Figure 5:
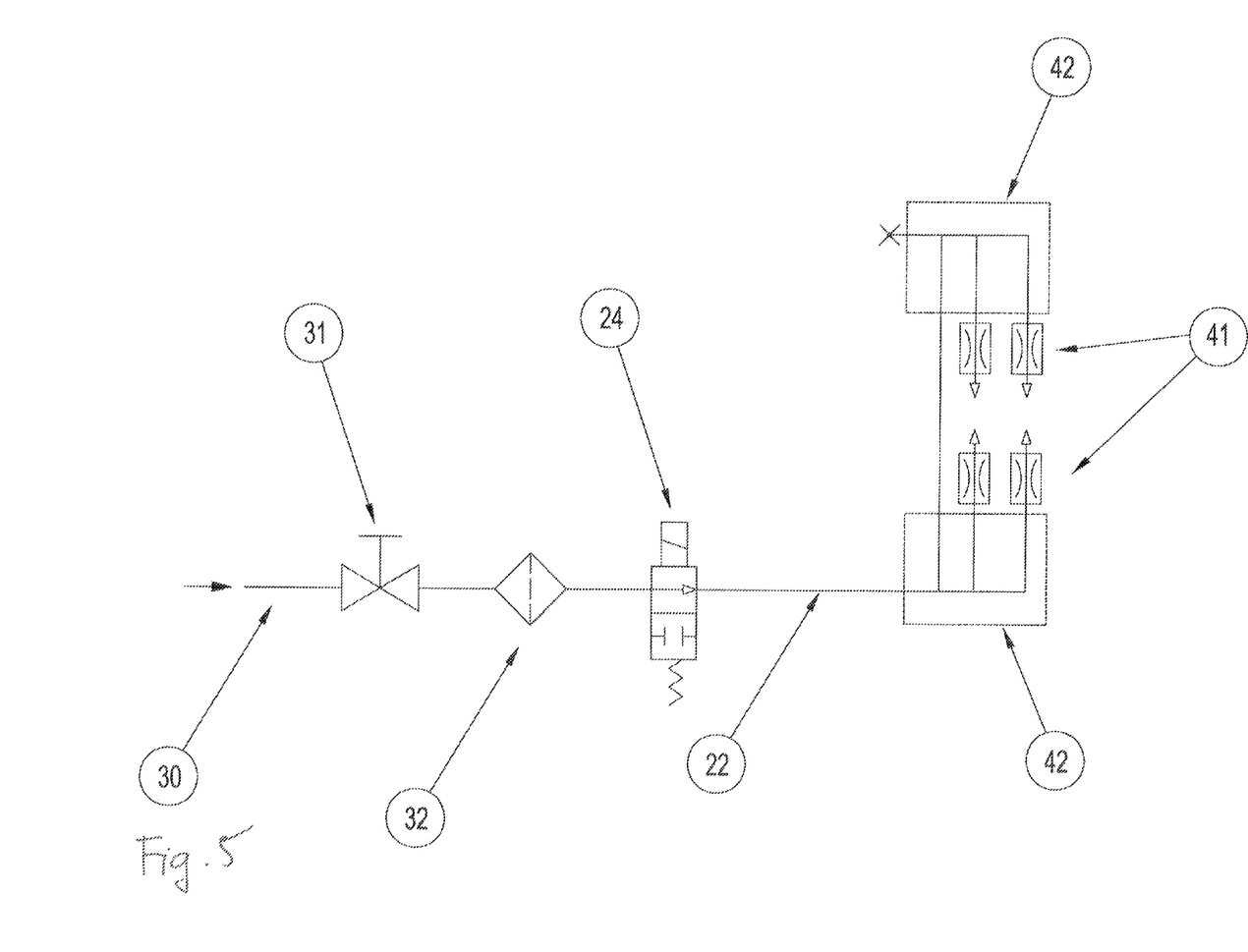
FIG. 5 is a schematic view of a water-supply circuit of the relative-humidity sensor apparatus of FIG. 1.

As shown in FIGS. 2 and 5, the jets 41 are preferably mounted on opposite sides of the thermocouple 16. In the illustrated embodiment, the jets 41 are paired to provide four different jets 41. The jets 41 are supported by a manifold 42 (e.g., built in aluminum) that feeds the pressurized water from the water-supply line 22.

The jets 41 may be any suitable type of jet. According to an embodiment, two of the jets 41 are flat-spray jets, whereas two other jets 41 are cone-spray jets. The flat-spray jets produce a spray of greater pressure to clean the sock 18, whereas the cone-spray jets are used to humidify the sock 18. Any other combination is considered as well, as a function of the process, and type of dust particles that could contaminate the sock 18.

An outlet 43 is aligned with a longitudinal axis of the thermocouple 16 and allows the thermocouple 16 to extend out of the casing 11 to reach the measuring position in which the sock 18 projects outside of the casing 11. The outlet 43 may be a swivel-type coupling, with a male end welded to the casing 11 in register with the throughbore in the casing 11, while a female end may be connected to a support plate by which the sensor apparatus 10 is supported. Alternatively, the outlet 43 may be screwed to the casing 11, and may be any appropriate type of coupler.

Referring to FIG. 3, a drain 44 is provided in a bottom of the washing compartment 14, and is connected to a drain pipe for the evacuation of the washing water typically containing dust particles.

Figure 4:
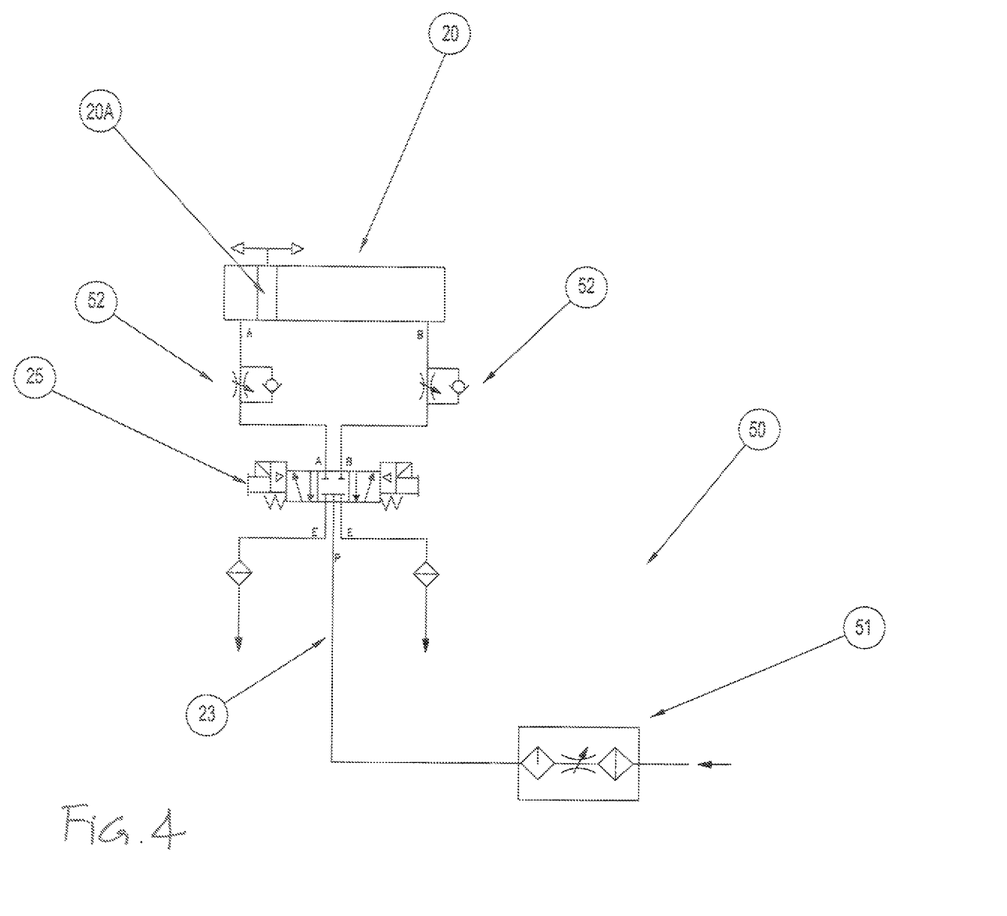
FIG. 4 is a schematic view of an air-supply circuit of the relative-humidity sensor apparatus of FIG. 1.

Referring to FIG. 4, a pneumatic circuit is illustrated at 50, showing the displacement of the carriage 20A of the linear actuator 20. A lubricating unit 51 is positioned in the air-supply line 23, to ensure the proper conditions of the compressed air in terms of pressure, filtration and/or lubricant content.

The valve 25 is connected to a controller of the sensor apparatus 10, and controls the actuation of the linear actuator 20. According to an embodiment, the valve 25 is a 4-way pneumatic solenoid valve (e.g., Parker B5 series) operating 3 positions, namely open, close and neutral, although a 2 position valve could be used as well. Appropriate valves 52 may be provided upstream and/or downstream (as shown in FIG. 4) of the linear actuator 20, to control the velocity of the carriage 20A of the linear actuator 20. The valves 52 are flow control valves. Either one of the downstream valve sets and the upstream valve sets may be removed. It is considered to equip the linear actuator 20 with flow controllers to ensure that the thermocouple 16 moves between the measuring position and the washing position.

Figure 6:
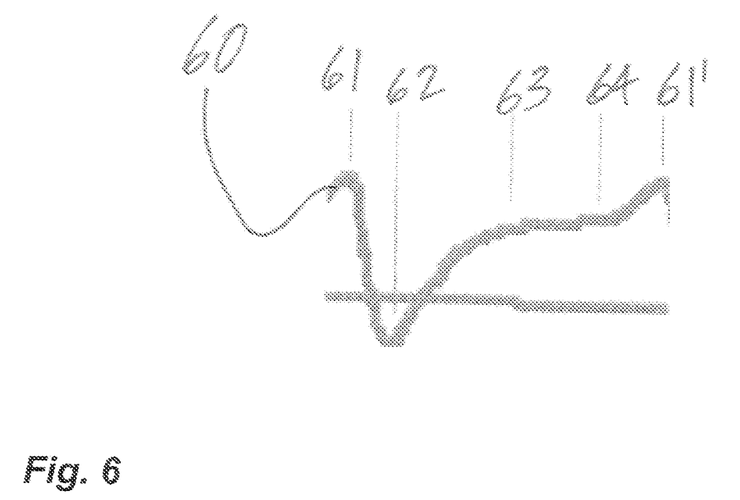
FIG. 6 is a graph showing a wet bulb temperature measurements as measured using the relative-humidity sensor apparatus of FIG. 1.
Figure 7:
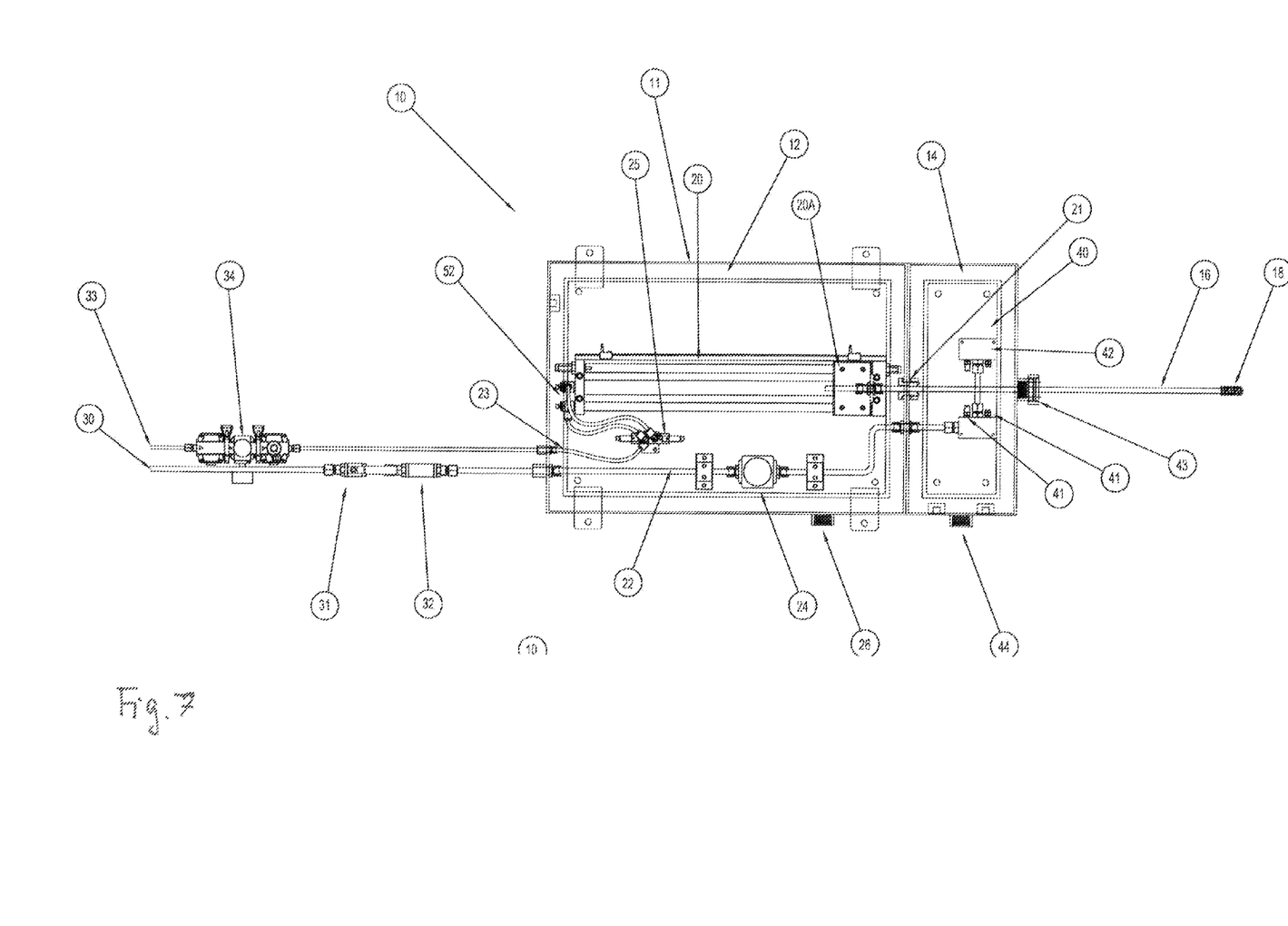
FIG. 7 is a top plan view of the relative-humidity sensor apparatus of FIG. 1, with the thermocouple in a measuring position.
Figure 8:
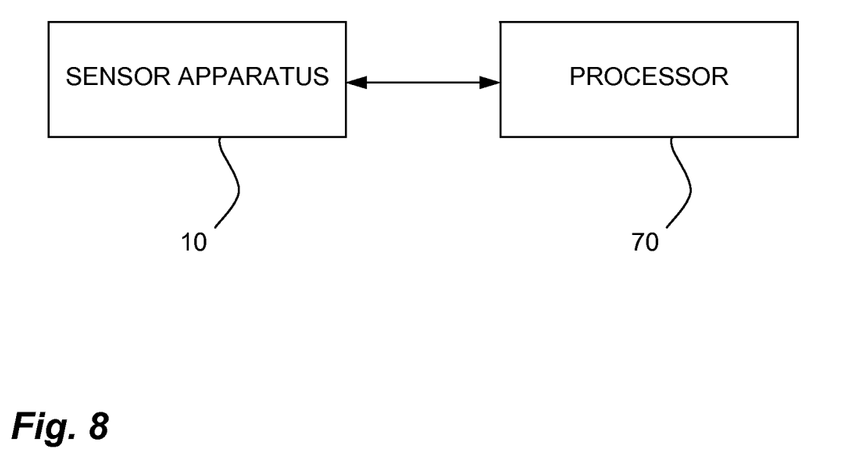
FIG. 8 is a schematic view of a system featuring the relative-humidity sensor apparatus of FIG. 1.

Referring to FIG. 6, there is illustrated a wet bulb temperature reading at 60, for one cycle. The temperature reading 60 drops from 61 to 62, and this represents the movement of the thermocouple 16 from the measuring position to the washing position, and the washing, cooling and humidifying of the sock 18 of the thermocouple 16. At 62, the sock 18 of the thermocouple 16 is reinserted in the measuring environment (e.g., oven) by reaching the measuring position. From 62 to 63, the water on the sock 18 heats up and reaches at 63 the wet bulb temperature of the air, for a given period of time as shown by the plateau from 63 to 64. From 64 to 61', the sock dries, resulting in an increase in the temperature measurement. Accordingly, a new washing cycle may be performed starting at 61'. In order to detect the end of the plateau 63-64 period, the temperature is continuously monitored, and a rate of temperature increase beyond a given threshold will trigger the switch of the sensor apparatus 10 to a washing mode. The sensor apparatus 10 is therefore coupled to a processor 70 (FIG. 8). The processor 70 may take any appropriate format, and outputs the wet bulb temperature, and possibly the dry bulb temperature and relative humidity, among numerous other parameters (e.g. historical data, cycles, etc.).

Therefore, the method for measuring the wet-bulb temperature comprises humidifying the sock 18 and positioning the sock in an environment in which the wet-bulb temperature is monitored. The wet-bulb temperature is measured by the processor 70, which processor 70 may also control the operation of the sensor apparatus 10. An effective wet-bulb temperature by monitoring a rate of change of the wet-bulb temperature to detect a low change threshold simultaneously with the measuring. A dry condition of the sock is identified by monitoring a rate of change of the wet-bulb temperature to detect a high change threshold simultaneously with the measuring and sequentially after the low change threshold.

The wet bulb temperature measurements are therefore taken intermittently. However, due to the continuous monitoring of the temperature measurements, the cycles may be shortened to wash the sock 18 of the thermocouple 16 when the sock 18 is dry, beyond 64 of the temperature measurement (FIG. 6). Moreover, considering that the process parameters may vary over monitoring, the identification of the plateau 63-64 allows the optimization of the measurements.

Any appropriate controller may be used to operate the sensor apparatus 10 and control its various components (e.g., linear actuator 20 through valve 25), washing unit 40 through valve 24, thermocouple 16. For instance, a Eurotherm™ 3504 controller is one of numerous controllers that can be used to operate the sensor apparatus 10, and to calculate relative humidity from the dry-bulb and wet-bulb temperature readings.

With the above-described configuration, the relative humidity sensor apparatus 10 is well suited for high-temperature oven or drier applications in heavy industrial applications. The sensor apparatus 10 could be used in the pulp and paper industry, in the treatment of biomass, smelter processes, bitumen-treatment processes, among numerous other possibilities. Although the sensor apparatus 10 is shown with a single one of the measuring devices (i.e., thermocouple 16), there may be other such devices in the same translational arrangement as the thermocouple 16.

Moreover, the use of the controller with the sensor apparatus 10 ensures that process parameters are measured with greater precision, thereby allowing adjustments to the process parameters for optimizing the process.

The invention claimed is:

1. A sensor apparatus for measuring wet-bulb temperature, comprising:
   a casing;
   a measuring device comprising a sock at its probe end;
   a washing unit having at least one fluid outlet in the casing for projecting a fluid on the sock to remove residue and to humidify the sock; and
   a linear actuator displacing the measuring device between a washing position in which the sock is in register with the washing unit in the casing, and a measuring position in which the measuring device has the sock out of the casing and away from the washing unit to measure an ambient wet bulb temperature, the linear actuator being a pneumatic magnetically-coupled rodless actuator, with an end of the measuring device being secured to a carriage of the rodless actuator.

2. A sensor apparatus for measuring wet-bulb temperature, comprising:
   a casing:
   a measuring device comprising a sock at its probe end;
   a washing unit having two outlets opposite one another in the casing for projecting a fluid on the sock to remove residue and to humidify the sock, with the sock being positioned between the two fluid outlets in the washing position; and
   an actuator displacing the measuring device between a washing position in which the sock is in register with the washing unit in the casing, and a measuring position in which the measuring device has the sock out of the casing and away from the washing unit to measure an ambient wet bulb temperature.

3. The sensor apparatus according to claim 2, wherein the two fluid outlets are flat spray jets.

4. A sensor apparatus for measuring wet-bulb temperature, comprising:
   a casing:,
   a measuring device comprising a sock at its probe end;
   a washing unit having four fluid outlets, with pairs of the fluid outlets being opposite one another in the casing for projecting a fluid on the sock to remove residue and to humidify the sock, with the sock being positioned between the pairs of two fluid outlets in the washing position; and
   an actuator displacing the measuring device between a washing position in which the sock is in register with the washing unit in the casing, and a measuring position in which the measuring device has the sock out of the casing and away from the washing unit to measure an ambient wet bulb temperature.

5. The sensor apparatus according to claim 4, comprising a pair of the fluid outlets being flat-spray jets to wash the sock, and another pair of the fluid outlets being cone-spray jets to humidify the sock.

6. A sensor apparatus for measuring wet-bulb temperature, comprising:
   a measuring device comprising a sock at its probe end;
   a washing unit having at least one fluid outlet for projecting a fluid on the sock to remove residue and to humidify the sock;
   a casing comprising a washing compartment enclosing the washing unit, and a mechanical compartment enclosing an actuator, with a generally watertight partition between the compartments; and
   the actuator displacing the measuring device between a washing position in which the sock is in register with the washing unit in the casing, and a measuring position in which the measuring device has the sock out of the casing and away from the washing unit to measure an ambient wet bulb temperature.

7. The sensor apparatus according to claim 6, wherein the measuring device has an elongated shaft, and wherein the casing comprises a guiding sleeve between the washing compartment and the mechanical compartment with the elongated shaft being threaded through the guiding sleeve.

8. The sensor apparatus according to claim 7, further comprising a wiper seal on the guiding sleeve.

9. The sensor apparatus according to claim 6, further comprising a drain in a bottom of the washing compartment to collect liquid.

10. The sensor apparatus according to claim 6, further comprising a drain in a bottom of the mechanical compartment to collect liquid.

11. A sensor apparatus for measuring wet-bulb temperature, comprising:

a casing:

a measuring device comprising a sock at its probe end;

a washing unit having at least one fluid outlet in the casing for projecting a fluid on the sock to remove residue and to humidify the sock; and an actuator displacing the measuring device between a washing position in which the sock is in register with the washing unit in the casing, and a measuring position in which the measuring device has the sock out of the casing and away from the washing unit to measure an ambient wet bulb temperature;

wherein the measuring device has an elongated shaft, and wherein the casing comprises a coupler in an outer wall, with the elongated shaft being threaded through the coupler to extend out of the casing in the measuring position.

12. The sensor apparatus according to claim 11, wherein the coupler is a swivel-type coupler.

13. The sensor apparatus according to claim 1, further comprising another measuring device to measure an ambient dry-bulb temperature.

* * * * *